US011007055B2

(12) United States Patent
Centola et al.

(10) Patent No.: US 11,007,055 B2
(45) Date of Patent: May 18, 2021

(54) INTRALUMINAL VASCULAR PROSTHESIS FOR IMPLANTATION INTO THE HEART OR CARDIOVASCULAR VESSELS OF A PATIENT

(71) Applicant: NVT AG, Muri AG (CH)

(72) Inventors: Marcos Centola, São Paulo (BR); Emilia Kawa, Haigerloch (DE); Maximilian Kuetting, Boeblingen (DE)

(73) Assignee: NVT AG, Muri AG (CH)

( * ) Notice: Subject to any disclaimer, the term of this patent is extended or adjusted under 35 U.S.C. 154(b) by 118 days.

(21) Appl. No.: 16/391,405

(22) Filed: Apr. 23, 2019

(65) Prior Publication Data
US 2019/0254817 A1    Aug. 22, 2019

Related U.S. Application Data

(63) Continuation of application No. PCT/EP2017/077044, filed on Oct. 24, 2017.

(30) Foreign Application Priority Data

Oct. 24, 2016  (DE) ..................... 20 2016 105 963.1

(51) Int. Cl.
*A61F 2/24* (2006.01)
*A61F 2/91* (2013.01)
(Continued)

(52) U.S. Cl.
CPC .............. *A61F 2/2418* (2013.01); *A61F 2/07* (2013.01); *A61F 2/91* (2013.01); *A61F 2/90* (2013.01);
(Continued)

(58) Field of Classification Search
CPC ............. A61F 2/24; A61F 2/2418; A61F 2/91
(Continued)

(56) References Cited

U.S. PATENT DOCUMENTS 8,747,461 B2 *  6/2014  Centola ................. A61F 2/2418
                                                  623/2.19
9,445,896 B2    9/2016  Straubinger et al.
                (Continued)

FOREIGN PATENT DOCUMENTS

CN     104274259 A    1/2015
CN     104470579 A    3/2015
(Continued)

OTHER PUBLICATIONS

Office Action (Including Machine Translation) for corresponding Chinese Application No. 201780066034.2, dated May 25, 2020.
(Continued)

*Primary Examiner* — Suzette J Gherbi
(74) *Attorney, Agent, or Firm* — Jason H. Vick; Sheridan Ross, PC

(57) ABSTRACT

The present invention concerns an intraluminal vascular prosthesis for implantation into the heart and/or cardiac vessels of a patient, in particular for anchoring in the region of the cardiac valve leaflets. The vascular prosthesis comprises a stent support and a prosthesis material at least partially covering the stent support, such, that a covered proximal portion and a non-covered distal portion are formed. Furthermore, the vascular prosthesis has at least one elongate wire-shaped anchoring structure at the proximal end, which is substantially loop-shaped and which is fixed at two ends to the stent support and which is positioned with its proximal end in the form of a loop pointing in the proximal direction and projecting beyond the proximal end of the stent support.

11 Claims, 4 Drawing Sheets

(51) Int. Cl.
*A61F 2/07* (2013.01)
*A61F 2/90* (2013.01)

(52) U.S. Cl.
CPC ............... *A61F 2220/0008* (2013.01); *A61F 2230/0026* (2013.01); *A61F 2250/0098* (2013.01)

(58) Field of Classification Search
USPC ............................... 623/2.1–2.19, 1.15–1.16
See application file for complete search history.

(56) References Cited

U.S. PATENT DOCUMENTS

| | | | | |
|---|---|---|---|---|
| 9,474,604 | B2* | 10/2016 | Centola | A61F 2/2418 |
| 9,693,860 | B2* | 7/2017 | Sandstrom | A61F 2/2412 |
| 9,839,517 | B2* | 12/2017 | Centola | A61F 2/2418 |
| 10,219,896 | B2* | 3/2019 | Sandstrom | A61F 2/2412 |
| 10,226,344 | B2* | 3/2019 | Eidenschink | A61F 2/966 |
| 10,492,910 | B2* | 12/2019 | Kirk | A61F 2/2475 |
| 10,512,539 | B2* | 12/2019 | Centola | A61F 2/2436 |
| 10,722,316 | B2* | 7/2020 | Zeng | A61F 2/0095 |
| 2002/0138135 | A1* | 9/2002 | Duerig | A61F 2/2475 |
| | | | | 623/1.24 |
| 2003/0236568 | A1* | 12/2003 | Hojeibane | A61F 2/2415 |
| | | | | 623/1.24 |
| 2005/0096734 | A1* | 5/2005 | Majercak | A61F 2/2475 |
| | | | | 623/1.24 |
| 2005/0096735 | A1* | 5/2005 | Hojeibane | A61F 2/2418 |
| | | | | 623/1.24 |
| 2008/0036113 | A1* | 2/2008 | Chun | A61F 2/2412 |
| | | | | 264/177.14 |
| 2008/0140189 | A1* | 6/2008 | Nguyen | A61F 2/2412 |
| | | | | 623/2.11 |
| 2011/0125258 | A1* | 5/2011 | Centola | A61F 2/2418 |
| | | | | 623/2.38 |
| 2015/0164662 | A1 | 6/2015 | Tuval | |
| 2015/0265402 | A1* | 9/2015 | Centola | A61F 2/2436 |
| | | | | 623/2.18 |
| 2016/0158007 | A1* | 6/2016 | Centola | A61F 2/2427 |
| | | | | 623/1.26 |
| 2016/0256270 | A1 | 9/2016 | Folan et al. | |
| 2017/0172737 | A1* | 6/2017 | Kuetting | A61F 2/2418 |
| 2017/0245862 | A1* | 8/2017 | Cox | A61F 2/86 |
| 2017/0273785 | A1* | 9/2017 | Seguin | A61F 2/2433 |

FOREIGN PATENT DOCUMENTS

| | | |
|---|---|---|
| CN | 104921843 A | 9/2015 |
| CN | 105496607 A | 4/2016 |
| CN | 105658180 A | 6/2016 |
| DE | 10301026 A1 | 2/2004 |
| EP | 2724690 B1 | 7/2016 |
| WO | WO 01/49213 | 7/2001 |
| WO | WO 2009/094188 | 7/2009 |
| WO | WO 2013/134214 | 9/2013 |
| WO | WO 2013/183060 | 12/2013 |
| WO | WO 2015/061021 | 4/2015 |

OTHER PUBLICATIONS

Notice of Reasons for Refusal (Including Machine Translation) for corresponding Japanese Patent Application No. 2019-521708, dated Jul. 28, 2020.
International Preliminary Report on Patentability (Including Translation) for International Application No. PCT/EP2017/077044, dated Apr. 25, 2019.
International Search Report (Including Translation) for International Application No. PCT/EP2017/077044, dated Jan. 2, 2018.
Written Opinion for International Application No. PCT/EP2017/077044, dated Jan. 2, 2018.
International Preliminary Report on Patentability for International Application No. PCT/EP2017/077044, dated Oct. 25, 2018.

* cited by examiner

INTRALUMINAL VASCULAR PROSTHESIS FOR IMPLANTATION INTO THE HEART OR CARDIOVASCULAR VESSELS OF A PATIENT

CROSS REFERENCES TO RELATED APPLICATIONS

This application is a continuation of international patent application PCT/EP2017/077044, filed on Oct. 24, 2017 and designating the U.S., which international patent application has been published in German language and claims priority from German utility application DE 20 2016 105 963.1, filed on Oct. 24, 2016. The entire contents of these priority applications are incorporated herein by reference.

BACKGROUND

The present invention relates to an intraluminal vascular prosthesis for implantation into the heart and/or cardiovascular vessels of a patient, in particular for anchoring in the region of the cardiac valve leaflets; the vascular prosthesis has a distal and a proximal end, as well as a stent support and a prosthesis material with which the stent support is at least partially covered, so that a covered proximal section and a non-covered distal section are formed.

In general, state-of-the-art intraluminal vascular prostheses are used in particular for the treatment of aneurysms or to replace or support natural vessels or even heart valves.

An aneurysm is an arterial dilatation or arterial ballooning in which the cross-section of blood vessels widens locally in the shape of a spindle or bag as a result of congenital or acquired wall changes. Vascular prostheses are used to treat aneurysms. A distinction is made between a real aneurysm, a false aneurysm and a dissecting aneurysm (Aneurysm dissecans), which occurs as a result of a dissection of the vessel wall. The latter is a splitting of the wall layers of the aorta, which is usually caused by a tear in the inner vessel wall, with subsequent bleeding between the layers. Risk factors that can lead to aortic dissection include structural weakness of the vascular wall and arteriosclerosis.

Aortic dissection is usually immediately life-threatening because it can lead to aortic rupture and acute circulatory disorders of various organs. An immediate diagnosis of this disease is therefore of crucial importance.

Statistically, aortic dissections occur most frequently (approx. 65%) only a few centimetres above the aortic valve, in the ascending section of the aorta (Aorta ascendens). The second most frequent (approx. 20%) aortic dissections occur immediately after the left subclavian artery (Arteria subclavia sinistra) branching off in the descending section of the aorta (Aorta descendens). Furthermore, the aortic arch is affected with 10% or the abdominal artery (Aorta abdominalis) with 5%.

Depending on the local occurrence of a dissection, it is classified as "A" or "B", whereby a strict distinction has been made between aortic dissections with and without the involvement of the ascending aorta. Usually dissections in which the entry is in the area of the ascending aorta are called type A dissections, and dissections in which the entry is distal to the left subclavian artery are called type B dissections. As mentioned earlier, aortic dissection is one of the most urgent emergencies in cardiology and heart surgery. The high mortality rate of one to two percent per hour in the case of type A dissection in the acute phase requires an immediate clarification of the suspected diagnosis.

In an acute dissection of type A, it is therefore extremely important to quickly avert the danger of aortic rupture, whereby artificial vascular prostheses are currently commonly used for immediate surgical replacement of the Aorta ascendens. In emergency cases, however, reconstructions of the aortic valve are less common. As a rule, the aortic valve is therefore removed during dissection of the aortic sections close to the valve and in patients with congenital connective tissue disease, and a prosthesis with integrated valve prosthesis is inserted, to which the coronary vessels are also "connected" again. Basically, there are two types of heart valve prostheses: mechanical valves on the one hand, which are manufactured artificially and consist mainly of metal, and biological valves on the other hand, which are available as transplants from humans or animals.

The artificial prostheses can be introduced either via open surgery or minimally invasive.

The correct insertion of the prosthesis at the site to be treated regularly poses a challenge to the attending physician, as even a slight shifting of the prosthesis can re-integrate the "immobilised" aneurysm into the blood circulation, and thus the danger of rupture is present again. The risk of shifting or migration of the prosthesis is also present after its placement, especially in view of the natural heart movement. For these reasons, the prosthesis is usually fixed proximal and distal to the vessel wall with sutures. However, this suture fixation has the disadvantage that the vascular walls, which are often impaired anyway, are further strained. In patients with severely damaged vessel walls, fixation by suturing is also not possible.

Against this background, the object of the present invention is to provide a device with which the described disadvantages can be overcome and heart valve prostheses can be securely fixed in the heart, especially in type A dissections.

SUMMARY

According to the invention, this is solved by a vascular prosthesis of the type mentioned at the beginning, wherein the vascular prosthesis has at least one elongate wire-shaped anchoring structure at the proximal end, which is substantially loop-shaped, and which is fixed or attached distally via two ends to the stent support and whose proximal end points loop-shaped in proximal direction and is positioned projecting beyond the proximal end of the stent support.

In this way, the object underlying the invention is completely solved.

The specific anchoring structure of the vascular prosthesis provided at the proximal end ensures that it is securely anchored in the heart without disturbing the natural function of the heart valves. This is achieved by the specific design of the anchoring structure, which extends at the proximal end loop-like or arch-like in proximal direction. The vascular prosthesis can be positioned safely and specifically via this anchoring structure.

The vascular prosthesis according to the invention then serves as an anchor for a separately inserted cardiac valve prosthesis which is released at least partially or overlappingly in the vascular prosthesis according to the invention anchored in the vessel and which serves to support or replace the natural vascular prosthesis.

Each heart valve prosthesis can be inserted via the vascular prosthesis according to the invention, which heart valve prosthesis preferably has a self-expanding support with valves attached thereon. As an example, reference is made to EP 2 724 690, in which examples of heart valves are disclosed. The expert will be able to retrieve from the available information which heart valves are suitable for use with the vascular prosthesis according to the invention.

The anchoring structure ensures that an additional suturing of the vascular prosthesis or the cardiac valve prosthesis to the vessels and, thus, a straining of theses vessels can be avoided. The vascular prosthesis according to the invention thus represents a kind of anchor structure or receptacle structure through which the heart valve prosthesis to be inserted in a second step can be securely anchored in the heart. This also prevents complicated fixation elements from having to be provided on the heart valve prosthesis itself in order to fix it securely in the heart.

The anchoring structure is preferably positioned behind a leaflet of the aortic valve, preferably the non-coronary leaflet or "non-coronary cusp "NCC", while the vascular prosthesis itself and via its remaining body is still fixed in the catheter by means of a withdrawal sheath or other compression. This allows the anchoring structure to be precisely aligned and prevents subsequent proximal migration of the prosthesis.

The vascular prosthesis according to the invention is preferably used for the treatment of type A aortic dissections and is inserted minimally invasively via catheter-guided application.

In general, the terms "distal" and "proximal" are used for vascular prostheses or endoluminal stent grafts in general and in the present case to designate the respective ends of the vascular prosthesis, whereby the term "distal" refers to the part or end which lies further downstream in relation to the blood flow. The term "proximal", on the other hand, refers, again in relation to the blood stream, to a part or end that is further upstream in relation to the blood stream. In other words, the term "distal" means in the direction of the blood stream, and the term "proximal" means in the opposite direction of the blood stream. In the case of catheters, on the other hand, the term "distal" refers to the end of the catheter or delivery system that is inserted into the patient or that is the farthest away from the user, and the term "proximal" refers to the end that is closer to the user.

According to the invention, the classification of the basic body of the vascular prosthesis into a proximal section and a distal section means that the respective sections differ from each other in their construction and, for example, have a different number of stent rings or different length of the stent support, or their stent rings/stent support have different diameters, and/or are covered by prosthesis material ("covered") or uncovered ("uncovered"). The prosthetic material may be sutured or shrunk on or otherwise attached (fixed) to the stent support, either on the side of the stent support facing the vessel wall or on the inner side facing the blood flow.

The "covered" proximal section covered by prosthesis material should bridge the dissection, the un-covered distal section is placed distally of the dissection and serves mainly—like the covered section—to fix the vascular prosthesis in the vessel.

A "wire-shaped, substantially loop-shaped" anchoring structure presently means that the structure is formed by bending a wire or wire-like structure into an arc with two "free" ends and an arc end opposite the two free ends. "Free ends" means that these are not—like the arc section—directly or in one piece connected with each other.

"Substantially/substantial" also means that the anchoring structure does not have to be exactly loop-shaped and curved, but should only be designed in the manner of a loop and still be regarded as such by an expert.

According to the invention, the anchoring structure protrudes beyond the proximal end of the vascular prosthesis towards/in the proximal direction, the anchoring structure extending beyond the proximal end of the vascular prosthesis with between approx. 1 cm and 3 cm, preferably with approx. 1, 1.5, 2, 2.5 or 3 cm.

The prosthetic material may comprise or be formed from a material selected from polyester, polyurethane, polystyrene, polytetrafluoroethylene, ultra-high molecular weight polyethylene (UHMPE), or mixtures thereof.

A "stent support" is understood to be any wire prosthesis in the form of a tube or cylinder made of metal or synthetic fibre, preferably self-expanding, which forms a lattice or net-like framework/support to which a prosthesis material can be attached. This can be, for example, a wire network, or meandering, circumferential, so-called stent-springs/stent-rings, which are arranged one behind the other and which are, as the case may be, connected to each other by wire connecting struts, or which are only "connected" to each via by the implant material. The stent support is usually made of a shape memory material, usually nitinol, which allows the support to return to its expanded state after insertion into a vessel for release, thereby "stretching" the vascular implant.

Accordingly, according to an embodiment of the present invention, the stent support is a laser-cut stent support or a braided or woven stent support, or consists, if necessary only partially, (e.g. in the proximal section or in the distal section) of individual stent rings indirectly connected only via the prosthesis material and not directly to each other (by struts, bars or the like).

Taking into account the dissection to be dealt with and the state of the vessel, it will be clear and obvious for the expert which stent support will be used to achieve the best possible realisation of the invention. Accordingly, the proximal section may have a different stent support structure than the distal section of the vascular prosthesis, or both may have the same stent support.

Correspondingly, in a preferred embodiment, the stent support has diamond-shaped cells or consists of rows of diamond-shaped cells arranged one behind the other, which adjoin or are connected to each other via their corners. At the outermost ends of the vascular prosthesis there are proximal and distal correspondingly free "corners" of the diamond-shaped cells.

According to an embodiment of the vascular prosthesis according to the invention, fixation structures are provided at the distal end of the vascular prosthesis, via which the distal end of the vascular prosthesis can be fixed to and be held compressed by a release catheter. Preferably, the fixation structures are T-shaped extensions of at least three free corners of the diamond-shaped cells at the distal end. These T-shaped structures can engage with/in corresponding T-shaped recesses in the release catheter. A retraction sheath, which is then placed over the distal end of the vascular prosthesis, holds the T-shaped fixation structures in the T-shaped recesses and thus fixes the distal end of the vascular prosthesis to the release catheter. When the retraction sheath compressing the vascular prosthesis is retracted over the T-shaped recesses, the T-shaped fixation structures can detach from the recesses, releasing the distal end of the vascular prosthesis.

In an embodiment of the vascular prosthesis according to the invention, it is preferred if the distal ends of the wire-shaped anchoring structure are positioned at immediately adjacent corners of two diamond-shaped cells of the proximal end of the vascular prosthesis.

This embodiment ensures that the anchoring structure is stably "stretched" and that the loop is not enlarged, which could result in migration of the vascular prosthesis. The comparatively tight fixation of the distal ends of the loop provides rigidity to the anchoring structure via the proximal loop, which in turn ensures stable anchoring of the vascular prosthesis.

In another embodiment, it is preferred if the wire-shaped anchoring structure comprises a trapezoidal extension at its proximal end or end region.

Due to the trapezoidal extension, the anchoring structure receives additional stability in this area, with which the secure anchoring in the vessel wall is additionally secured.

According to further embodiment, it is preferred if the outermost proximal end of the wire-shaped anchoring structure is drop-shaped.

This design leads to an even better stability of the anchoring structure. "Drop-shaped" means that an additional small loop pointing in the proximal direction is imposed onto the "basic" loop-shape of the anchoring structure.

In the intraluminal vascular prosthesis according to the invention, and according to an embodiment it is preferred if the stent support and the anchoring structure are formed in one piece.

"One-piece" means that the stent support and the anchoring structure are made of the same wire or the same lasered tube.

In a development of the vascular prosthesis according to the invention, one, two or three anchoring structures are provided at the proximal end of the stent support.

By providing more than one anchoring structure, the vascular prosthesis can be fixed even more securely into the heart. The additional anchoring structures preferably have the same structure and shape, or different shapes; in these cases, however, the loop-shaped basic structure is common to all of them.

According to a further development of the intraluminal vascular prosthesis according to the invention, it is preferred if the stent support and/or the wire-shaped anchoring structure have hooks or spikes on its respective side facing away from and/or towards the vessel wall.

With these designs, the fixation of the vascular prosthesis in the vessel is further enhanced and secured. The hooks and/or spikes may be made of the same material as the anchoring structure or stent support, or of different materials.

In the embodiment of the hooks/spikes provided on the inner side of the vascular prosthesis, it is advantageous that these hooks/spikes further enhance the anchoring of a heart valve prosthesis to be at least partially inserted therein. Although the partial release and "tightening" of the cardiac valve prosthesis in the proximal end of the vascular prosthesis according to the invention already ensures its anchoring in the vascular prosthesis, the spikes and hooks can additionally support the anchoring of the cardiac valve in the vascular prosthesis.

According to a further embodiment of the intraluminal vascular prosthesis according to the invention, it is preferred if the stent support and/or the wire-like anchoring structure comprises X-ray markers.

The provision of x-ray markers on the anchoring structure facilitates the correct placement of the anchoring structure, and, thus, of the vascular prosthesis as a whole for the operating physician, as he can precisely place the vascular prosthesis into the heart under x-ray control.

The intraluminal vascular prosthesis according to the invention preferably has a diameter of between approx. 20 mm and approx. 48 mm, preferably between 24 mm and approx. 44 mm.

According to one embodiment, the diameter of the vascular prosthesis is essentially/substantially constant over its entire length.

In a further development of the intraluminal vascular prosthesis according to the invention it is preferred if it further comprises a cardiac valve prosthesis, wherein the cardiac valve prosthesis is designed in such a way that it can be released with its distal end at the proximal end of the intraluminal vascular prosthesis and can be fixed via it in the region of the cardiac valves.

In this embodiment there are two prostheses which together represent a system for the treatment of aortic dissection, in particular a type A dissection, according to the invention: As mentioned above, the vascular prosthesis according to the invention provides an anchoring structure which is fixed into the heart in a first step and via which a heart valve prosthesis which is inserted in a second step can be securely anchored into the heart. This avoids the risk of the heart valve prosthesis shifting or migrating and at the same time achieves a relatively simple structure of the system.

Further advantages can be taken from the figures and the following description of preferred embodiments.

It goes without saying that the features mentioned above and those still to be explained below can be used not only in the combination indicated, but also in other combinations or alone, without leaving the scope of this invention.

BRIEF DESCRIPTION OF THE DRAWINGS

Embodiments of the invention are shown in the drawing and are explained in more detail in the following description, which show.

DETAILED DESCRIPTION OF PREFERRED EMBODIMENTS

Figure 1:
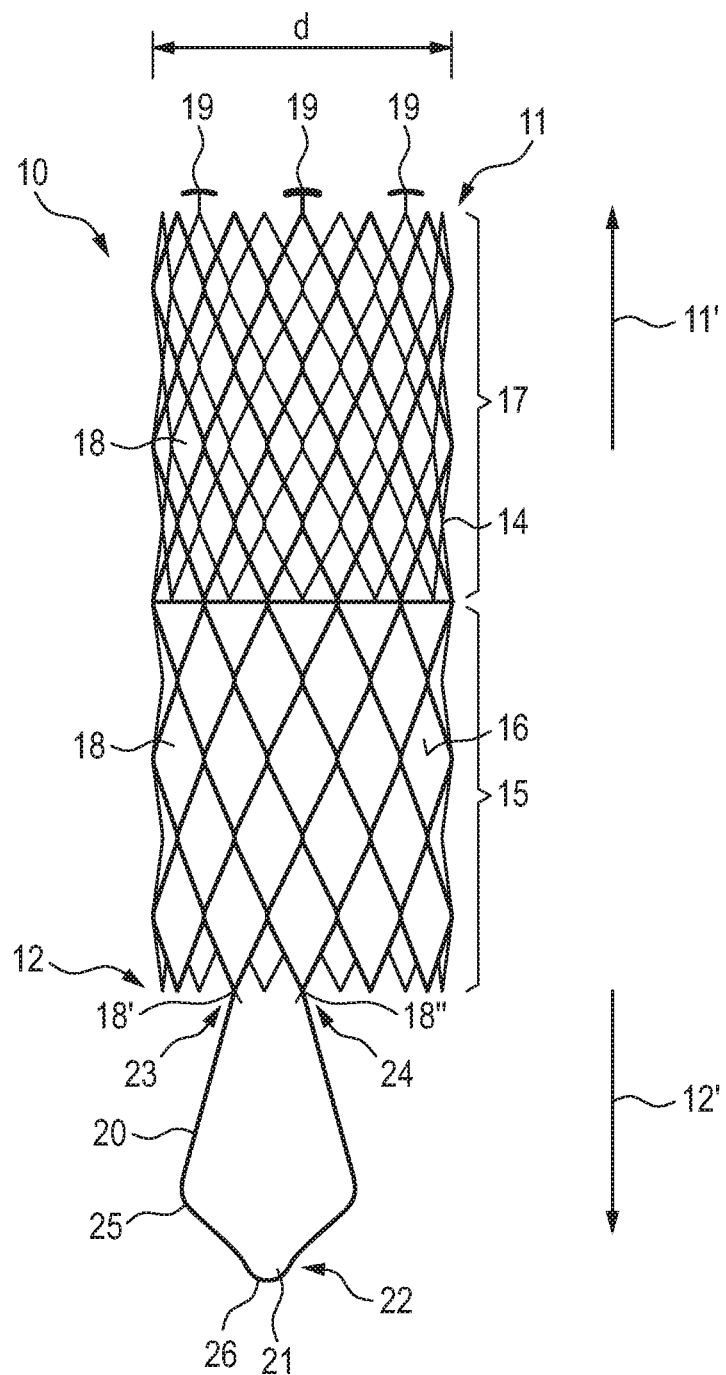
FIG. 1 is a schematic representation of an embodiment of a vascular prosthesis according to the invention, in the non-introduced, expanded state in a view of the longitudinal side.

In the figures, the same features are marked with the same reference signs, whereby for reasons of clarity not all reference signs are always indicated in all figures.

In FIGS. 1 to 4, reference sign 10 denotes an inventive vascular prosthesis as such, having a distal end 11 and a proximal end 12. The vascular prosthesis has a tubular stent support 14 to which a prosthesis material 16 is attached in a proximal portion 15, thereby covering the proximal portion 15. The vascular prosthesis 10 further comprises a distal section 17 which is free of prosthesis material.

According to the invention, the stent support 14 can be a laser-cut stent-support, or a woven or braided stent support consisting of several wires, or of single, meandering stent rings arranged one behind the other, which are (indirectly) connected to each other only via the prosthesis material.

In the example shown in the figures, the vascular prosthesis 10 has 18 diamond-shaped cells, which form the tubular or cylindrical stent support 14 in a row-like fashion. At the distal end 11, fixing structures 19 are provided at three free corners of the diamond-shaped cells 18 at the distal end 11, via which the distal end 11 of the vascular prosthesis 10 can be received in a release catheter (not shown) in corresponding receptacles or recesses and fixed to the release catheter via a withdrawal sheath (not shown) provided thereover. The fixation structures 19 are T-shaped as shown in FIG. 1.

A wire-shaped anchoring structure 20 is provided at the proximal end 12 of the vascular prosthesis 10, forming a loop 21 in/towards the proximal direction 12'. The anchoring structure 20 is approx. ⅓ of the total length of the vascular prosthesis 10 and extends beyond its proximal end 12.

The anchoring structure 20 has a proximal end 22 with loop 21 formed in the area of the end 22. The anchoring structure 20 further comprises two distal ends 23 and 24 fixed or integral with two free corners 18', 18" of the diamond-shaped cells 18 at the proximal end 12 of the vascular prosthesis.

As shown in FIG. 1, the distal ends 23, 24 of the anchoring structure 20 are attached to/integrally with the immediately adjacent corners of the diamond-shaped cells 18 at the proximal end 12 of the vascular prosthesis 10.

Here, "free ends" of the diamond-shaped cells mean, as for any other embodiment of the vascular prosthesis according to the invention, that these corners are not connected to another diamond-shaped cell, but protrude freely in the distal direction 11' or proximal direction 12'.

FIG. 1 also shows that the anchoring structure 20 in the area of loop 21 has a trapezoidal extension 25 pointing towards the outside. This means that the distance between the distal ends 23, 24 of the anchoring structure 20 in the area of its fixation/attachment to the proximal end 12 of the vascular prosthesis 10 is smaller than the distance between the opposite wires of loop 21 in the proximal area 22.

As shown in FIG. 1, the anchoring structure 20 has an outermost drop-shaped proximal end 26 in its loop 21.

The anchoring structure 20 and the stent support 14 can be formed in one piece, e.g. by laser cutting a corresponding tube or cylinder.

The anchoring structure 20 and/or stent support 14 may have hooks or spikes (not shown) on their respective side facing away from the vessel wall and may include one or more x-ray markers.

The diameter d of the vascular prosthesis according to the invention is preferably between 20 mm and 48 mm, preferably between approx. 24 mm and approx. 44 mm.

Figure 2A:
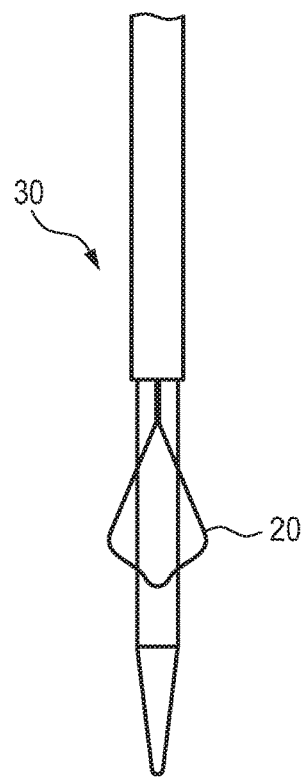
FIGS. 2A, 2B, and 2C are schematic representations of the stepwise release of the vascular prosthesis of FIG. 1, with a schematically depicted release catheter; in the fully charged state (A); with partially retracted compression structure but with the proximal and distal end of the vascular prosthesis still fixed to the release catheter (B); and with released proximal end (C)

FIG. 2 schematically shows the release of a vascular prosthesis 10 loaded on a release catheter 30. The vascular prosthesis 10 is fixed to the release catheter at its distal end 11 via the fixation structures 19 provided there in corresponding recesses and by covering it with a withdrawal sleeve 31. The vascular prosthesis 10 is also detachably fixed via its proximal end 12 to the release catheter 30 via a corresponding system (not shown). The fully fixed and compressed state of the vascular prosthesis 10 is shown in FIG. 2A.

Figure 2B:
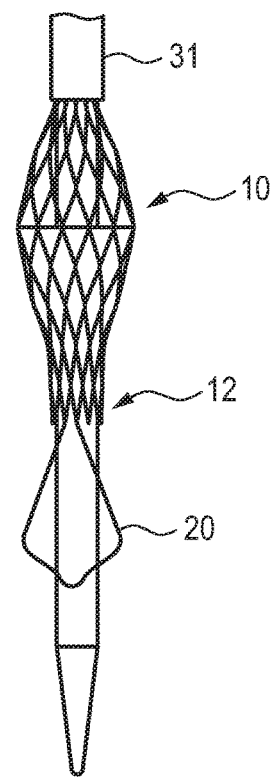

After retraction of the retraction sheath 31 which keeps the vascular prosthesis compressed, a central area of the vascular prosthesis 10 expands balloon-like, while the proximal and distal ends 12, 11 of the vascular prosthesis 10 are still fixed to the release catheter 30 (see FIG. 2B).

Figure 2C:
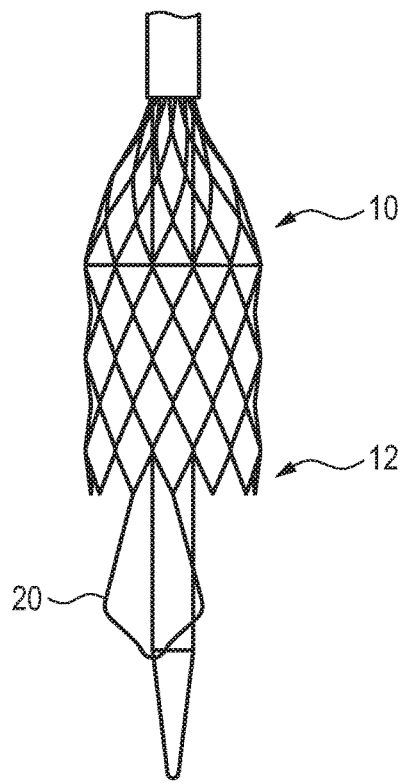

After the release of the proximal end 12 of the vascular prosthesis 10, it can expand, whereas the distal end 11 of the vascular prosthesis 10 is still fixed and compressed at the release catheter 30 and through the withdrawal sheath 31 (see FIG. 2C). In this state, the vascular prosthesis 10 according to the invention can be released and positioned at the desired location, preferably behind a leaflet of the aortic valve (see also FIG. 3), preferably behind the non-coronary leaflet or "non-coronary cusp "NCC". This allows the anchoring structure 20 to be precisely aligned and prevents subsequent proximal migration of the vascular prosthesis.

Figure 3:
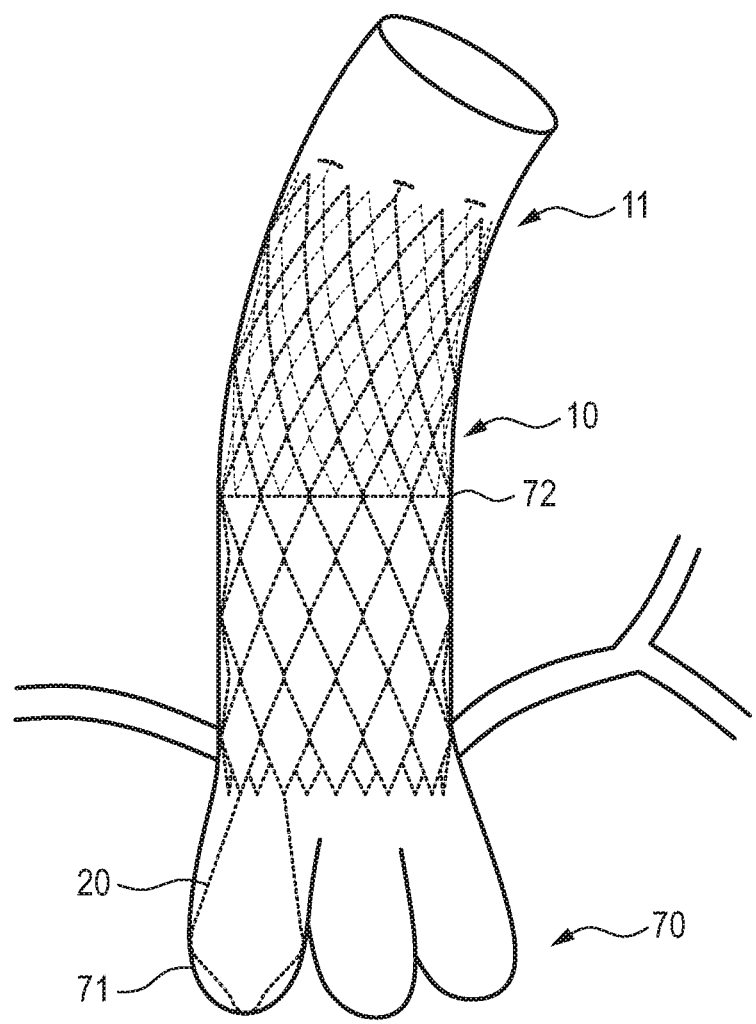
FIG. 3 is the schematic representation of an embodiment of the vascular prosthesis according to the invention completely released in the cardiovascular system.

If the positioning of the anchoring structure 20 is secured, the remaining vascular prosthesis can be released by completely retracting the retraction sheath 31. The completely released state of the vascular prosthesis 10 in a heart 70 is shown in FIG. 3, in which figure the vascular prosthesis is shown in dashed lines for a better overview. It can be seen here that the anchoring structure 20 is positioned behind a leaflet of the aortic valve 71, while the rest of the vascular prosthesis 10 extends distally into/towards the ascending aorta 72.

Figure 4:
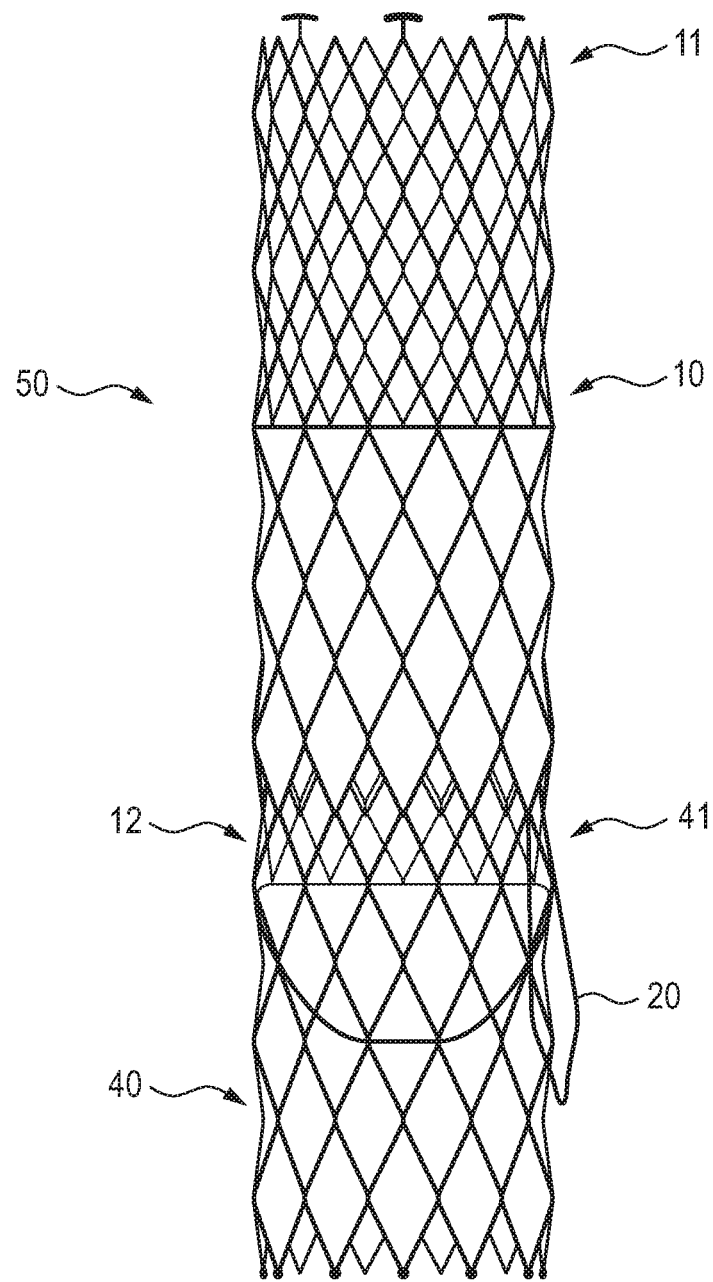
FIG. 4 shows a schematic representation of a system according to the invention, with a heart valve prosthesis anchored in a vascular prosthesis according to the invention, the representation being shown outside the heart vessel.

Finally, FIG. 4 shows a system 50 according to the invention consisting of a vascular prosthesis 10 and a heart valve prosthesis 40 in assembled form, outside the heart for better overview.

As soon as the vascular prosthesis 10 is positioned as an anchor in the heart, the heart valve prosthesis 40 can be inserted over it and released in such a way that the heart valve prosthesis 40 with its distal end 41 in the vascular prosthesis 10 at least partially engages at its proximal end 12 or is already fixed there by expansion.

What is claimed is:

1. An intraluminal vascular prosthesis adapted for implantation into a heart and/or into cardiovascular vessels of a patient, for anchoring in a region of cardiac valve leaflets, the vascular prosthesis having a distal and a proximal end, the vascular prosthesis having a stent support, and a prosthesis material with which the stent support is at least partially covered, such that a covered proximal portion and a non-covered distal portion are formed, wherein the vascular prosthesis comprises, at the proximal end, at least one elongate wire-shaped anchoring structure which is loop-shaped and which via two ends is fixed to the stent support and which is positioned with its proximal end in the form of a loop pointing towards the proximal direction and projecting beyond the proximal end of the stent support, wherein the distal ends of the wire-shaped anchoring structure are positioned at immediately adjacent corners to two diamond-shaped cells.

2. The intraluminal vascular prosthesis according to claim 1, wherein the wire-shaped anchoring structure comprises a trapezoidal extension in a region of the loop.

3. The intraluminal vascular prosthesis according to claim 1, wherein an outermost proximal end of the wire-shaped anchoring structure is drop-shaped.

4. The intraluminal vascular prosthesis according to claim 1, wherein the stent support is a laser-cut stent support or a braided or woven stent support.

5. The intraluminal vascular prosthesis according to claim 1, wherein the stent support and the anchoring structure are integrally formed.

6. The intraluminal vascular prosthesis according to claim 1, wherein one to three anchoring structures are provided at the proximal end of the stent support.

7. The intraluminal vascular prosthesis according to claim 1, wherein the stent support and/or the wire-shaped anchoring structure have hooks or spikes on their respective side facing away from the vascular wall.

8. The intraluminal vascular prosthesis according to claim 1, wherein the stent support has hooks or spikes on its side facing the vascular wall.

9. The intraluminal vascular prosthesis according to claim 1, wherein the stent support and/or the wire-shaped anchoring structure comprises X-ray markers.

10. The intraluminal vascular prosthesis according to claim 1, wherein the vascular prothesis has a diameter of between approx. 20 mm to approx. 48 mm, preferably of between 24 mm to approx. 44 mm.

11. The intraluminal vascular prosthesis according to claim 1, further comprising a heart valve prosthesis, wherein the heart valve prosthesis is configured to be released with its distal end at the proximal end of the intraluminal vascular prosthesis and can be fixed via the latter in the region of the heart valves.

* * * * *